United States Patent [19]
Gandolfi et al.

[11] Patent Number: 4,845,113
[45] Date of Patent: Jul. 4, 1989

[54] 2-SUBSTITUTED-1,4-DIHYDROPYRIDINES AND PHARMACEUTICAL COMPOSITIONS CONTAINING THEM

[75] Inventors: Carmelo A. Gandolfi; Marco Frigerio; Silvano Spinelli; Odoardo Tofanetti; Ernesto Menta; Sergio Tognella, all of Milan, Italy

[73] Assignee: Boehringer Biochemia Robin S.p.A., Milan, Italy

[21] Appl. No.: 889,377

[22] Filed: Jul. 25, 1986

[30] Foreign Application Priority Data

Aug. 19, 1985 [IT] Italy .................................. 21944 A/85

[51] Int. Cl.$^4$ .................. C07D 211/86; A61K 31/455
[52] U.S. Cl. .................................... 514/356; 544/365; 544/131; 544/405; 514/252,318,332,333,334,338,336,344,352; 546/193; 546/194; 546/256; 546/257; 546/263; 546/270; 546/278; 546/281; 546/283; 546/284; 546/286; 546/310; 546/316; 546/321; 546/322
[58] Field of Search ................ 546/321, 283, 193, 284, 546/194, 286, 256, 310, 257, 316, 263, 322, 270, 278, 281; 544/365, 336; 514/252, 344, 318, 352, 332, 356, 334, 338

[56] References Cited

U.S. PATENT DOCUMENTS 4,492,703  1/1985  Goldman et al. .................... 546/321
4,532,248  7/1985  Franckowiak et al. ............. 514/344

FOREIGN PATENT DOCUMENTS 0123850  11/1964  European Pat. Off. .

OTHER PUBLICATIONS

Angelova, I. et al., Chemical Abstracts 96:162501y.
Kubo et al. Arch. Int. Pharmiodyn 272, 282-295 1984.
Franckowiak, et al "The Optical Isomers . . ." *European Journal of Pharmacology*, 114 (1985) pp. 223-226.
Seidel, Wolfgang, "QSAR and Molecular . . ." 2nd European Seminar & Exhi. on Computer Aided Molecular Design.
Hof, R. P. et al "Stereoselectivity at the . . ." *Journal of Cardiovascular Pharmacology*, 1985 pp. 689-693.
Schachtele, C. et al "Stereoselective Inhibition . . ."
Naunyn-Schmiedeberg's Arch. of Phar. 1987, pp. 340-343.
Three Onoda Papers to Wayne State University.
Honn, et al, "Calcium Channel . . ." Proceedings of the Soc. for Exptl. Biology & Medicine 174, (1983) pp. 16-19.
Onoda J. et al, "Cisplatin and Nefedipine . . ." Cancer Letters 3 (1986) pp. 181-188.
Onoda, J. et al, "Calcium Channel Blockers . . ." Hemostatic Mec & Metastasis Martinus-Nighoff, The Hague, 1984 pp. 207-226.
Onoda, J. et al, "Antithrombogenic Effects of Calcium . . ." Thrombosis Research 34; 1984, pp. 367-378.
Bossert, F. et al, "4-Aryldihydropyridines, a New . . ." Angew. Chem. Int. Ed. Engl. 20.762-769 (1981).
Angelova, et al., Chemical Abstracts 96:162501y.
Halliwell Faseb Journal 1, 358-364, 1987.
Halliwell Ed. "Oxygen Radicals and Tissue Injury", 1988.
McCall et al. Acta Anaesthesiologica Belgira 38, 373-379 (1987).
Del Maestro, Acta Physiol. Scan. Supp. 492, 153-168.
Simpson et al, J. Lab. Clin. Med. 110, 13-30 (1987).
Abst. from "International Conference on Oxygen, Free Radicals in Health Disease", 1988.

*Primary Examiner*—Jane T. Fan
*Attorney, Agent, or Firm*—Armstrong, Nikaido Marmelstein Kubovcik & Murray

[57] ABSTRACT

Compounds of formula I

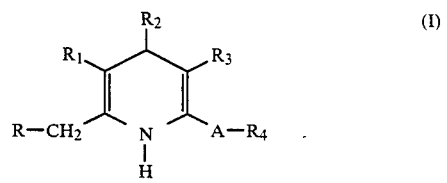

wherein R is hydrogen or lower alkyl; $R_1$ is acetyl, benzoyl, cyano, nitro, carboxy, alkoxycarbonyl or aminocarbonyl groups; $R_2$ is an optionally substituted aryl or hetaryl residue; $R_3$ is a carboxy or alkoxycarbonyl group; A is a cyclopropyl group or a group of formula —CH=CH— and $R_4$ is a phenyl or heteroaryl group, optionally mono, di or tri-substituted, are useful in radical scavenging therapy.

7 Claims, No Drawings

2-SUBSTITUTED -1,4-DIHYDROPYRIDINES AND PHARMACEUTICAL COMPOSITIONS CONTAINING THEM

The present invention relates to 2-substituted-1,4-dihydropyridines, to a method for their preparation and to pharmaceutical compositions containing them.

The compounds of the invention have the following formula I:

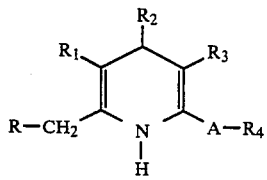

wherein

R is hydrogen or $C_1-C_5$ lower alkyl;

$R_1$ is a member selected from the group consisting of acetyl, benzoyl, cyano, nitro, free or esterified carboxy group of formula $CO_2R_5$, amide of formula $-CONR_6R_1$;

$R_2$ represents:
(a) a phenyl group unsubstituted or substituted by one or more $C_1-C_6$ alkyl, $C_1-C_6$ alkoxy, halo-$C_1-C_6$ alkyl, halo-$C_1-C_6$ alkoxy, halogen, nitro, cyano, $C_1-C_6$ alkoxycarbonyl, $C_1-C_6$ alkylthio, $C_1-C_6$ alkylsulphinyl groups;
(b) pentafluorophenyl;
(c) α or β-naphthyl;
(d) a five or six-membered-heterocyclic ring;
(e) α-benzo-[2,3-b]-1,4-dioxane, or
(f) α-benzo[3,4-c]-fluroxanyl;

$R_3$ is a free or esterified carboxy group of formula $CO_2R_5$; A is a group of formula

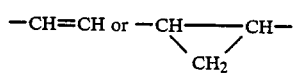

in cis or in trans form;

$R_4$ is a member selected in the group consisting of:
(a) a phenyl ring unsubstituted or substituted by one or more halogen atoms, hydroxy, mercapto, $C_1-C_4$ alkoxy, $C_1-C_4$ alkylthio, $C_2-C_{12}$ acyloxy, imidazol-1-yl, $-NO_2$, amino, monoalkylamino or dialkylamino groups;
(b) a five or six-membered-heterocyclic ring unsubstituted or substituted by hydroxy, $C_1-C_4$ alkoxy, amino, carboxyamide, acetoxy groups or $C_1-C_4$ alkyl groups;

$R_5$ is hydrogen; a $C_1-C_6$ alkyl chain unsubstituted or substituted by hydroxy, amino, monoalkylamino, dialkylamino groups or $C_1-C_6$ alkoxy groups; $C_3-C_6$ alkenyl; an optionally substituted aryl or $C_1-C_4$ aralkyl group; an ammonium or alkaline metal cation;

$R_6$ and $R_7$, which are the same or different, may be hydrogen, $C_1-C_6$ alkyl, benzyl or aryl.

Also the pharmaceutically acceptable salts as well as the optical antipodes, i.e. the enantiomers, the racemic mixtures of the optical antipodes, the geometric isomers and their mixtures and the mixtures of the diastereoisomers of the compounds of formula (I) are included in the scope of the invention.

Dihydropyridines derivatives having an unsubstituted cyclopropyl group in 2 or 6 position are known from Japan Kokai No. 78 95976: said derivatives are not only structurally different but also have a different pharmacological behaviour in comparison with the compounds of the invention.

FR No.-2435471 discloses dihydropyridines derivatives having, inter alia, in 2 position an ethenyl group optionally substituted by an halogen or by cyano, hydroxy or lower alkyl groups. Structural and pharmacological differences are evident also in this case.

In the compounds of formula I the alkyl, alkenyl, alkoxy and alkanoyloxy groups are branched or straight chain groups.

A halo-$C_1-C_6$ alkyl group is preferably trihalo-$C_1-C_6$ alkyl, in particular trifluoromethyl.

A halo-$C_1-C_6$ alkoxy group is preferably $OCHF_2$.

A $C_1-C_6$ alkyl group is preferably methyl, ethyl, isopropyl and tert-butyl.

A $C_3-C_6$ alkenyl group is preferably allyl.

A monoalkylamino radical is preferably a methyl, ethyl, isopropyl and benzylamino group.

A dialkylamino group is preferably a dimethylamino, diethyl, benzyl-, methylamino group.

A dialkylamino group is more preferably a radical wherein the dialkyl substituent is part of a cyclic radical such as pyrrolidin-1-yl, piperidin-1-yl, piperazin-yl-, 4-substituted-pyrazin-1-yl, imidazol-1-yl, 2-alkoxycarbonyl-pyrrolidin-1-yl.

Particularly preferred dialkylamino groups are diethylamino, morpholin-4-yl, 4-methyl-pyperazin-1-yl, pyrrolidin-1-yl, piperidin-1-yl and imidazol-1-yl.

When $R_4$ is a heterocyclic ring, it is preferably a heteromonocyclic ring containing at least one heteroatom selected from the group consisting of N, S and O. When $R_2$ is a five or six membered heterocyclic ring, this residue is preferably pyridyl, furanyl and thienyl.

Specific examples of preferred compounds of the invention are:

2-(2-phenylethenyl)-3,5-dicarboethoxy-4-(m-nitrophenyl)-6-methyl-1,4-dihydropyridine;

2-[2-(4-hydroxyphenyl)ethenyl]-3,5-dicarboethoxy-4-(m-nitrophenyl)-6-methyl-1,4-dihydropyridine;

2-[2-(4-hydroxy-3-methoxyphenyl)-ethenyl]-3,5-dicarboethoxy-4-(m-nitrophenyl)-6-methyl-1,4-dihydropyridine;

2-(2-phenylethenyl)-3,5-dicarboethoxy-4-(o-trifluoromethylphenyl)-6-methyl-1,4-dihydropyridine;

2-(2-phenylethenyl)-3,5-dicarboethoxy-4-(2-methylthiophenyl)-6-methyl-1,4-dihydropyridine;

2-[2-(3-methoxy-4-hydroxy-5-N-morpholinomethylphenyl)-ethenyl]-3,5-dicarboethoxy-4-(m-nitrophenyl)-6-methyl-1,4-dihydropyridine;

2-[2-(4-imidazol-1-yl-phenyl)-ethenyl]-3,5-dicarboethoxy-4-(m-nitrophenyl)-6-methyl-1,4-dihydropyridine;

2-[2-(3-methoxy-4-hydroxy-5-N-pyrrolidinomethylphenyl)-ethenyl]-3,5-dicarboethoxy-4-(m-nitrophenyl)-6-methyl-1,4-dihydropyridine;

2-[2-(3-methoxy-4-hydroxy-5-imidazol-1-yl-methylphenyl)-etheny]-3,5-dicarboethoxy-4-(m-nitrophenyl)-6-methyl-1,4-dihydropyridine;

2-(2-phenylethenyl)-3-carboethoxy-5-cyano-4-(m-nitrophenyl)-6-methyl-1,4-dihydropyridine;

2-(2-phenylethenyl)-3-carboethoxy-5-nitro-4-(m-trifluoromethylphenyl)-6-methyl-1,4-dihydropyridine;

2-(2-mercaptophenylethenyl)-3,5-dicarboethoxy-4-(m-chlorophenyl)-6-methyl-1,4-dihydropyridine;

2-[2-(3-pyridyl)ethenyl]-3,5-dicarboethoxy-4-(m-nitrophenyl)-6-methyl-1,4-dihydropyridine;

2-[2-(3-methyl-2-thienyl)-ethenyl]-3,5-dicarboethoxy-4-(m-nitrophenyl)-6-methyl-1,4-dihydropyridine;

2-(2-phenyl-1-cyclopropyl)-3,5-dicarboethoxy-4-(m-nitrophenyl)-6-methyl-1,4-dihydropyridine;

2-[2-(3-pyridyl)-1-cyclopropyl]-3,5-dicarboethoxy-4-(m-trifluoromethyl)-6-methyl-1,4-dihydropyridine;

2-[2-(4-hydroxyphenyl)-1-cyclopropyl]-3,5-dicarboethoxy-4-(m-nitrophenyl)-6-methyl-1,4-dihydropyridine.

The compounds of the invention of formula I are obtained by a process comprising:

(a) cyclization of a compound of formula II

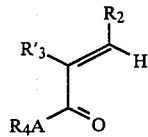
(II)

wherein $R_4$, $R_2$ and A are as above defined and $R'_3$ is an esterified carboxy group, with a compound of formula III

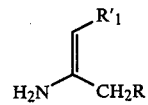
(III)

wherein $R'_1$ is acetyl, cyano, benzoyl, nitro, an esterified carboxy group or $-CONR_6R_7$ wherein R, $R_6$ and $R_7$ are as defined above, to give a compound of formula Ia

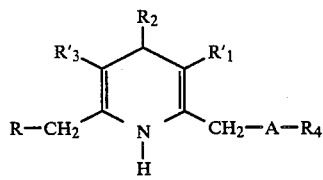
(Ia)

wherein R, $R'_1$, $R_2$, $R'_3$ and $R_4$ are as above defined; compounds Ia, if necessary, after removal of known protective groups possibly present in $R'_1$, $R'_3$, $R_4$, may be converted into a compound of formula I and/or, if desired, subjected to salification and/or isomers separation procedures; or (b) reaction of a phosphonium salt of general formula IV

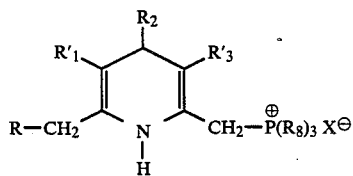
(IV)

wherein R, $R'_1$, $R_2$, $R'_3$ are as above defined, $R_8$ is n-butyl or phenyl, $X^-$ is chlorine, bromine or iodine, with an aldehyde of formula (V)

$R_4-CHO$ (V)

to give a compound of formula Ib

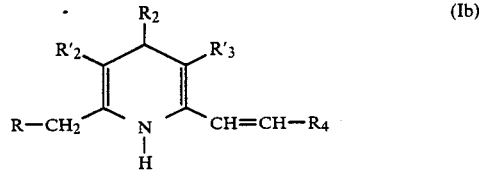
(Ib)

wherein R, $R'_1$, $R_2$, $R'_3$ and $R_4$ are as above defined; compounds Ib, after removal of known protective groups possibly present in $R'_1$, $R'_3$, $R_4$, may be subjected to esterification, etherification or reaction with dimethylsolfoxonium methylide to produce a compound of formula I wherein A is a cyclopropyl ring, which may be optionally subjected to saponification, esterification, salification and/or optical resolution.

The compounds of formula II are prepared by reaction of an aldehyde of formula V $R_2-CHO$ with a β-ketoester of formula VI

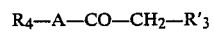
$R_4-A-CO-CH_2-R'_3$ (VI)

wherein $R_2$, $R'_3$ and $R_4$ are as above defined, using known procedures in the art, for example Knoevenagel reaction, i.e. refluxing the aldehyde and the β-ketoester in an inert solvent, e.g. benzene or toluene, in the presence of piperidine acetate or trifluoroacetate, removing the water formed during the reaction.

When the β-ketoesters of formula VI are unknown, compounds, they may be prepared using known methods starting from the known acids of formula VII

$R_4-A-CO_2H$ (VII).

An activated form of acid of formula VII (e.g. chloride, imidazolide) may be reacted with Meldrum acid or with the magnesium enolate of a malonic acid emiester. For more detailed illustrations of general methods for β-ketoester synthesis see for ex. Y. Oikawa et al., J. Org. Chem. 43, 2087 (1978), D. G. Melillo et al., Tetrah. Lett. 21, 2783 (1980) and D. C. Brooks et al., Angew. Chem. Int. Ed., 18, 72 (1979).

The acids of formula VII are disclosed in: A. Burger and W. L. Yost, JACS. 70, 2198 (1949), E. N. Trachtenberg and G. Odian, JACS 80, 4015 (1958), D. G. Markees and A. Burger, JACS 70, 3329 (1948), O. M. Nofedov et al., Angew. Chem. 89, 674 (1977), Gray and Kraus, JOC 31, 399 (1966), Cooper, Can. J. Chem. 48, 3882 (1970), A. Burger et al., JACS 71, 3307 (1949), J. W. McFarland, JOC 30, 3298 (1965), A. Burger et al., J. Med. Chem. 13, 33 (1970).

The cyclization of a compound II with a compound III may be carried out with either stoichiometric amounts or a small excess of the enamine of formula III in an inert solvent such as benzene, toluene, tetrahydrofuran, $CH_2Cl_2$, 1,2-dichloroethane, pyridine, acetic acid, $C_1-C_5$ lower alcohols, as well as mixtures thereof.

The reaction is preferably carried out at temperatures ranging from room temperature to the reflux temperature of the reaction mixture, preferably from 45° to 70° C.; the reaction times may vary from several days to few hours, but usually do not exceed four hours.

A reduction of the reaction time may be obtained by addition of catalytic amounts of an organic or inorganic acid such as hydrochloride, alkyl(aryl)sulphonic or acetic acid, to the cooled reaction mixture after 0.5-2 hours of heating.

The reaction of the phosphonium salt IV with an aldehyde V is carried out using either stoichiometric amount or a small excess of the aldehyde in the presence of a base. A stoichiometric amount of a base, at least, is necessary to generate "in situ" the ylide, which is the reactive species, from the phosphonium salt.

Such a base may be an alkaline or earth alkaline hydride, alcoholate, a lithium alkyl, lithium diisopropylamide, sodium amide, a tertiary amine, i.e. triethylamine, 2,2,2-diazabicyclo-octane, potassium or sodium carbonate.

Suitable solvents are $C_1$-$C_4$ lower alcohols, dimethylsulphoxide, dimethylformamide, linear or cyclic ethers e.g. dimethoxyethane, dioxane, tetrahydrofuran; and benzene as well as mixtures thereof.

The reaction is preferably carried out in a temperature range from $-30°$ C. to the reflux temperature of the reaction mixture, preferably from $-10°$ C. to room temperature; the reaction times may range from few minutes to several hours but usually do not exceed four hours.

The optional cyclopropanation reaction may be performed by addition of a compound of formula Ib to a solution of an excess of dimethylsolfoxonium methylide formed "in situ" by treatment of a dimethylsulphoxonium iodide with a base such as sodium hydride or butyllithium or tert-buOK in a suitable solvent, such as dimethylsulphoxide, tetrahydrofuran, dioxane, dimethylformamide as well as mixtures thereof at a temperature ranging from $-10°$ C. to $80°$ C.

Preferred compounds of the invention are compounds of formula (I) wherein $R_4$ is a mono or poly substituted phenyl or heterocyclic ring.

Preferred substituents are hydroxy, amino, thiol groups: as it is usual in preparative organic chemistry, in order to minimize side reactions or to make purification and crystallization processes easier, said substituents may be previously protected by groups removable selectively and under mild conditions, such as acetalethers, enolethers, silyl, methoxyethoxymethylethers, p-methoxybenzylethers for hydroxy and mercapto groups; amides and 3,5-dimethylpyrrol-1-yl for primary amines; tert-butyl, alkoxymethylester for carboxylic acids.

The protection and deprotection of said functional groups optionally present in $R_4$, $R'_3$, $R'_1$ of formula Ia and Ib are therefore comprised within the scope of the present invention.

Furthermore a free hydroxy, thiol, carboxy or amino group, when present in a compound of formula I, may be optionally converted into a protected functional group to make the purification process of the final compound easier.

The enamines of formula III are known compounds commercially available or easily preparable with known methods, for example by hydrogenolytic cleavage of known isoxazole precursors such as the compounds of formula VIII a-c

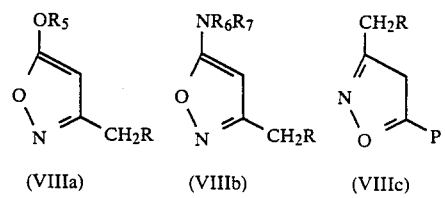

wherein R, $R_5$, $R_6$, $R_7$ are as defined above and P is methyl or phenyl.

The phosphonium salts of formula IV are described in Ital. Pat. Appln. No. 21875 A/85 in the applicant's name.

The aldehyde of formula V are known compounds commercially available or are prepared starting from known compounds and according to known methods. For example, starting from vanillin by Mannich reaction with a suitable dialkylamine and formaldehyde, 3-methoxy-4-hydroxy-5-dialkylaminomethyl-benzaldehydes V are prepared. Before of the Wittig reaction, the phenolic and thiophenlic groups of the aldehyde V are preferably protected. If desired, when $R_4$ is a phenyl substituted by hydroxy groups, the Mannich reaction with a suitable dialkylamine and formaldehyde or the equivalent reaction with an acylaminomethylene chloride may be postponed at the end of the synthetic procedure.

The salification of a compound of formula (I), the preparation of a free compound from a salt and the separation of the isomers from a mixture may be carried out by known methods.

The non toxic, pharmaceutically acceptable salts, include hydrochlorides, hydrobromides, hydroiodides, (lower)alkylsulfates, (lower)alkyl and aryl sulfonates, phosphates, sulfates, maleates, fumarates, succinates, tartrates, citrates, and others commonly used in the art.

The salts obtained through the variation of the acid used in some cases have special advantages dueto increased stability, increased solubility, decreased solubility, ease of crystallization, lack of objectionable taste, etc., but these are all subsidiary to the main physiological action of the free base, which is independent of the character of the acid used in the preparation of the salt.

The compounds of the invention are endowed with radical scavenging activity. The radical scavenging properties of the compounds of the invention is assessed according to R. Kubo et al. (Arch. Intern. Pharmacodyn., 272, 283, 1984), measuring the decrease of optical absorption of ethanol 0.1 mM solutions of 2,2-diphenyl-1-picrylhydrazyl, a stable free radical, used for photometric determination of $\alpha$-tocopherol.

Representative compounds of the invention are the compounds of formula I wherein $R_4$ is a phenyl ring substituted by free hydroxy, thiol and o- or p-positioned dialkylaminomethylene groups.

For most of them, when tested at a final 0.1 mM concentration, the decreases of the optical absorption after ten minutes at 517 nm range from 0.7 to 0.3 in comparison with a decrease in optical absorption of 0.7 for $\alpha$-tocopherol at 0.03 mM final concentration (see for example A. Mellors et al., J. Biol. Chem. 241, 4353, 1966).

The compounds of the invention are also able to protect cellular membranes from oxidative injuries, for example a reduced malondialdehyde formation is observed after incubation of rat erythrocyte membranes (M. Aishita et al., Arch. Intern. Pharmacodyn., 261, 316, 1983) and a rat brain homogeneate (Stocks et al., Clin. Sci. Molec. Med., 47, 215 (1974) with the compounds of the invention.

Using rabbit platelet rich plasma (PRP) in "in vitro" and "ex vivo" experiments, a reduced production of malondialdehyde is observed after challenge with arachidonic acids. The compounds of the invention are then able to interfere with the metabolic pathways of arachidonic acids and in particular with the lipoxygenase pathway, as shown using radioimmunoassay procedures, by a more pronounced reduced production of $LTB_4$ in comparison with $TXB_2$.

For example, in the presence of 6-methyl-3,5-dicarboethoxy-4-(m-nitrophenyl)-2-[(3-methoxy-4-hydroxy-5-N-morpholinomethylphenyl)-2-ethenyl]-1,4-dihydropyridine, a dose dependent decrease of malondialdehyde ranging from 75% to 25% is measured when a PRP pool of rabbits ($3.10^8$ platelets/ml) is challenged with arachidonic acid (2 mM final concentration) at a final concentration of the tested compound ranging from 1 mM to 0.1 mM.

More significantly, after oral administration of the same compound to male rabbits (20 mg/kg), an 87% decrease of malondialdehyde after 3 hours and a 44% decrease after 24 hours has been observed when a pool of collected PRP was challenged with arachidonic acid.

Binding receptorial studies with the compounds of the invention with cerebral rat brains show good affinities for 1,4-dihydropyridines sites.

Using "in vitro" rat aorta strips, according to Godfraind's procedure (see T. Godfraind et al., Arch. Intern. Pharmacodyn., 172, 235 (1968)) the compounds appear to be from modest to middle inhibitors of the calcium induced concentration, to the $K^+$-depolarized tissues.

Free radical generation and peroxidative degradation of cellular membranes is considered to be a major event involved in the ischemic damage (see for example Domopoulos et al., Acta Neurol. Scand. 56, Suppl. 64, 152–153, 1977). The experimental results obtained with the compounds of the invention after "in vitro" and "in vivo" test, allow to consider that they are particularly useful in human therapy as antiischemic agents in the treatment of myocardial renal and cerebral ischemias.

They can be also useful in the control of electrolyte fluxes through membranes of blood cellular components such as platelets, leukocytes, erithrocytes and in the regulation of their deformability and reactivity against excitatory stimuli: as a consequence they may be useful in the treatment of thromboembolic diseases, as protective agents against cellular membrane degradation, as antimetastatic agents and as cellular protecting agents during radiant therapy. To obtain the desired therapeutic effect, the compounds of the invention of the formula I may be administered to the patient in different way, alone or in pharmaceutical preparation by oral or parenteral route, i.e. intravenously or intramuscularly. A pharmaceutical composition suitable forthis purpose can be prepared according to the known techniques, as described for instance in "Remington's Pharmaceutical Sciences Handbook", Hack Publishing Company, U.S.A.

The administered amounts vary according to gravity of the treated disease and to the administration route. If administered orally, the quantity of the active principle administered varies from 0.01 mg/kg to 10 mg/kg of the patient's body weight pro die. If administered parenterally, the amount of active principle varies from 0.001 mg/kg to 5 mg/kg of paient's body weight pro die and it is preferably comprised between 0.01 mg/kg and 2 mg/kg of patient's body weight pro die.

A single dose for oral administration may contain for example from 0.05 to 100 mg of active principle. A single dose for parenteral administration may contain, for example, from 0.05 to 70 mg of active principle.

The compounds of the invention, because of their long lasting effect, may be administered once or twice a day; however repeated daily administrations could be—at least in some cases—desirable and may vary according to the patient's conditions or the administration route. The word "patient" means not only human beings, but generally warm-blooded animals.

For the oral administration, the compound may be formulated in solid or liquid preparations such as capsules, pills, tablets, powders, solutions, suspensions or emulsions. The unit dosage form may be the hard or soft gelatine capsule containing for instance lubricants and inert excipients such as lactose, saccharose or starch. Alternatively, the compounds of the invention may be administered as tablets, on carriers such as lactose, saccharose or starch in combination with binders such as starch itself or gelatin, disintegrating agents such as potato starch, or alginic acid, and lubricants such as stearic acid and magnesium stearate.

For parenteral administration the compounds of the invention may be administered in injectable forms, dissolved or suspended in pharmaceutically acceptable diluents, with a pharmaceutical carrier such as a sterile liquid such as water or an oil, with or without the addition of other pharmaceutically acceptable excipients. Oils which may be used in said preparations are of mineral, vegetal, animal or synthetic kind. Generally, as a carrier for injectable solutions the following substances may be used: water, salts, aqueous solutions, dextrose or other sugars aqueous solutions, ethanol, glycols such as propylenglycol and polyethylenglycols.

For the rectal administration, the compounds may be formulated in forms of suppositories, mixed with conventional vehicles such as, for example, cocoa butter, wax, polyvinylpyrrolidone or polyoxyethyleneglycols, or derivatives thereof.

The administration route generally preferred is the oral route, while the preferred pharmaceutical formulations are capsules.

The invention isillustrated by the following non limitative examples, wherein the abbreviations EtOH, DMSO, $Et_2O$, AcOEt refer to ethanol, dimethylsulfoxide, diethylether and ethylacetate respectively.

EXAMPLE 1

A solution of 2-phenyl-1-cyclopropanecarboxylic acid chloride (15 g) in 1,2-dichloroethane (70 ml) is added at 0° C. to a solution of 2,2-dimethyl-1,3-dioxane-4,6-dione (Meldrum's acid, 12 g) and pyridine (13.2 g) in 1,2-dichloroethane (70 ml) and the solution is stirred at room temperature for one hour. A 2N water solution of $H_2SO_4$ (20 ml) is then added, the two layers are separated and the organic phase is washed twice with water (50 ml), dryed on $Na_2SO_4$ and evaporated in vacuum. The residue is dissolved in EtOH (150 ml), heated to the reflux temperature for two hours and evaporated to dryness to give almost pure ethyl 3-(2-phenyl-1-cyclopropyl)-3-oxo-propanoate (21 g).

A solution of this compound (21 g), m-nitrobenzaldehyde (11 g), acetic acid (2 ml) and piperidine (0.5 ml) in benzene (100 ml) is heated to reflux in a Dean-Stark apparatus provided with a water separator, for two hours, then it is cooled to room temperature, washed with water (3×20 ml), dried on Na and evaporated to give, after column-chromatography, 15 g of ethyl-3-(2-phenyl-1-cyclopropyl)-2-(m-nitrophenylmethylen)-3-oxopropanoate as an oil.

NMR δ (CDCl$_3$): 1.2 (t, 3H, J=6 Hz); 1.6 (m, 2H); 2.3 (m, 2H); 4.1 (q, 2H, J=6 Hz); 7.15 (sb,6H); 8.10 (m, 4H).

EXAMPLE 2

Using in the procedure of Example 1 a 2-(substituted)-1-cyclopropane carboxylic acid chloride or 3-substituted acrylic acid chloride and a suitable aldehyde, the following 3-substituted-2-(phenylmethylen)-3-oxo-propanoates are obtained:

TABLE 1

$$\underset{O}{\overset{H}{\underset{\|}{\diagdown}}}\overset{R_2}{\underset{A-R_4}{\diagup}}\text{COOEt}$$

| R$_2$ | A | R$_4$ |
|---|---|---|
| m-Cl—C$_6$H$_4$ | ▽ | C$_6$H$_5$ |
| o-CF$_3$—C$_6$H$_4$ | ▽ | C$_6$H$_5$ |
| β-pyridyl | ▽ | C$_6$H$_5$—p-Cl |
| m-NO$_2$—C$_6$H$_4$ | ▽ | C$_6$H$_4$—p-OMe |
| m-NO$_2$—C$_6$H$_4$ | ▽ | C$_6$H$_4$—p-NH$_2$ |
| m-Cl—C$_6$H$_4$ | ▽ | C$_6$H$_4$—p-NO$_2$ |
| m-CF$_3$—C$_6$H$_4$ | ▽ | 2-pyridyl |
| o-NO$_2$—C$_6$H$_4$ | ▽ | pyrrolyl (N-H) |
| o-Cl—C$_6$H$_4$ | HC=CH | 3,4,5-trimethoxyphenyl (OCH$_3$) |
| m-NO$_2$—C$_6$H$_4$ | HC=CH | pyrrolyl (N-H) |

EXAMPLE 3

A solution of ethyl 3-(2-phenyl-1-cyclopropyl)-2-(m-nitrophenylmethylen)-3-oxo-propanoate (5 g) and ethyl-3-aminocrotonate (1.6 g) in EtOH (50 ml) is heated to the reflux temperature for 4 hours, then it is cooled at 0° C., acidified with concentrated aqueous HCl (0.2 ml) and stirred at 0° C. for 30 minutes. After neutralization with a few drops of a saturated Na$_2$HPO$_4$ water solution, the mixture is evaporated and the residue is dissolved in AcOEt (60 ml), washed with water (3×10 ml), dried on Na$_2$SO$_4$ and purified on silica gel (200 g, eluent: diisopropylether/Et ether/Et$_2$O 80/20) to give 4.0 g of 2-(2-phenyl-1-cyclopropyl)-3,5-dicarboethoxy-4-(m-nitrophenyl)-6-methyl-1,4-dihydropyridine amorphous solid.

NMR δ (CDCl$_3$): 1.2 (t, 3H, J=6 Hz); 1.3 (b octet, 4H, J=8 Hz); 2.4 (s, 3H); 4.2 (q, 4H, J=6 Hz); 5.2 (sb, 1H); 5.9 (sb, 1H); 7.2 (sb, 5H); 7.6 (m, 2H); 8.1 (m, 2H).

EXAMPLE 4

A solution of sodium ethoxide (0.52 g) in EtOH (20 ml) is added, at +10° C. under N$_2$ atmosphere, to a solution of [6-methyl-3,5-dicarboethoxy-4-(m-nitrophenyl)-1,4-dihydropyridin-2-yl]methyltriphenylphosphonium chloride (5 g) and benzaldehyde (0.8 g) in EtOH (50 ml). A deep purple coloration is observed, fading in 30 minutes, then the reaction mixture is neutralized with a few drops of a saturated solution of NaH$_2$PO$_4$, evaporated to dryness, the residue dissolved in Et$_2$O (80 ml), washed with water (3×20 ml), dried on Na$_2$SO$_4$, evaporated to dryness, and finally purified by silica gel column chromatography (180 g, eluent: Et$_2$O/diisopropyl ether 50/50) to give 4.2 g of 2-(2-phenyl)ethenyl-3,5-dicarboethoxy-4-(m-nitrophenyl)-6-methyl-1,4-dihydropyridine, m.p. 127°–128° C.

EXAMPLE 5

Using in the procedure of Example 3 an enamine selected from alkyl 3-aminocrotonate, 3-aminocrotononitrile, 3-nitro-2-amino-2-propene, 4-amino-3-penten-2-one, 3-amino-1-phenyl-2-butene-1-one and a suitable alkyl 2-(substituted)-3-oxo-propanoate, prepared according to Example 1, or using in the procedure of Example 4 an aldehyde selected from: 4-acetoxy-3-methoxybenzaldehyde, 4-acetoxy-3-methoxy-5-N-morpholinomethyl-benzaldehyde, 4-(2-methoxyethoxy)methoxy-3-methoxy-5-(4-methyl-piperazin-1-yl)methylbenzaldehyde, 4-(2-methoxyethoxy)-methoxy-3-methoxy-5-N-pyrrolidinomethylbenzaldehyde, 4-(2-methoxyethoxy)methoxy-3-bromo-5-methoxy-benzaldehyde, 4-nitro-benzaldehyde, 2-(2-methoxyethoxy)methylthiobenzaldehyde, 2-acetoxy-3-methoxybenzaldehyde, α-, β-, γ-pyridinecarboxyaldehyde, 2-furanal or 3-methyl-2-thiophenecarboxyaldehyde and a suitable (1,4-dihydropyrid-2-yl)-methylphosphonium salt the compounds listed in following Tables 2 and 3 are obtained.

TABLE 2

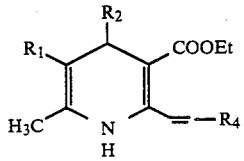

| $R_1$ | $R_2$ | $R_4$ | m.p. (°C.) or NMR DHP—CH=CH—$R_4$ signals (δ, TMS) |
|---|---|---|---|
| COOEt | m-$NO_2$—$C_6H_4$ | 2-OCH₃, 1-OCOCH₃-phenyl | 155–157° C. |
| COOEt | m-Cl—$C_6H_4$ | 2-OCH₃, 1-OCOCH₃-phenyl | δ 5.70 (1H, sb), 6.80 (1H, sb) |
| COOEt | β-pyridyl | 2-OCH₃, 1-OCOCH₃-phenyl | δ 5.70 (1H, sb), 6.80 (1H, sb) |
| COOEt | m-$NO_2$—$C_6H_4$ | 2-OCH₃, 1-OCOCH₃, 5-(morpholinomethyl)-phenyl | 188–190° C. |
| COOEt | m-$NO_2$—$C_6H_4$ | 2-OCH₃, 1-O$CH_2$O$CH_2CH_2$O$CH_3$, 5-(4-methylpiperazin-1-ylmethyl)-phenyl | 6.55 (2H, dd), J = 12 Hz |
| CN | m-$NO_2$ | 2-OCH₃, 1-O$CH_2$O$CH_2CH_2$O$CH_3$, 5-(4-methylpiperazin-1-ylmethyl)-phenyl | 6.52 (2H, dd), J = 12 Hz |
| $CO_2Et$ | m-$NO_2$—$C_6H_4$ | 2-OCH₃, 1-O$CH_2$O$CH_2CH_2$O$CH_3$, 5-(pyrrolidin-1-ylmethyl)-phenyl | 6.80 (2H, sb) |

TABLE 2-continued
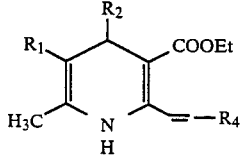
| R₁ | R₂ | R₄ | m.p. (°C.) or NMR DHP—CH=CH—R₄ signals (δ, TMS) |
|---|---|---|---|
| CO₂Me | m-CF₃—C₆H₄ |  | 6.80 (2H, sb) |
| CO₂Et | m-NO₂—C₆H₄ | 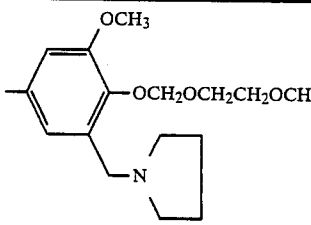 | 6.70 (2H, sb) |
| CO₂Et | m-NO₂—C₆H₄ | 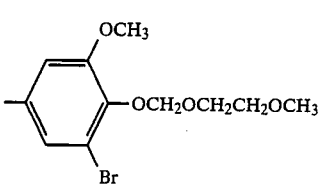 | 6.75 (2H, dd), J = 12 Hz AZ 109 |
| CO₂Me | m-Cl—C₆H₄ | 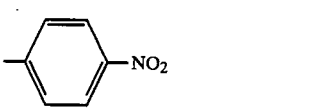 | 6.74 (2H, dd), J = 12 Hz |
| CO₂Et | m-NO₂—C₆H₄ | 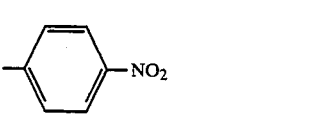 .HCl | 112–115° C. |
| CO₂Et | m-Cl—C₆H₄ | 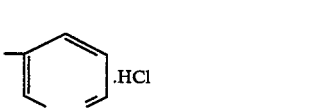 | 6.80 (2H, sb) |
| CO₂Et | m-CF₃—C₆H₄ | 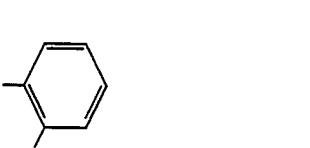 | 6.78 (2H, sb) |
| CO₂Et | m-NO₂—C₆H₄ | 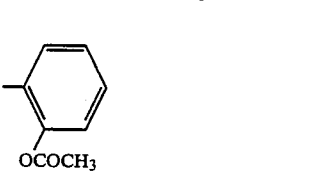 | 6.80 (2H, sb) |
| COOEt | o-CH₃S—C₆H₄ | C₆H₄ | 5.90 (1H, m), 7.00 (1H, m) |
| COOEt | o-NO₂—C₆H₄ | C₆H₄ | 5.90 (1H, m), 6.90 (1H, m) |
| NO₂ | m-CF₃—C₆H₄ | C₆H₄ | 6.00 (1H, m), 6.90 (1H, m) |
| COOEt | o-Cl—C₆H₄ | 3,4,5-tri(OCH₃)C₆H₄ | 5.70 (1H, m), 6.80 (1H, m) |

TABLE 2-continued

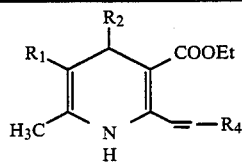

| | | | m.p. (°C.) or NMR DHP—⌢—R4 signals (δ, TMS) H · H |
|---|---|---|---|
| R1 | R2 | R4 | |
| COOEt | m-NO2—C6H4 | 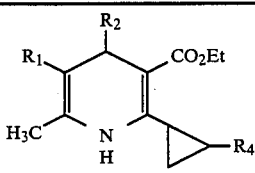 | 5.80 (1H, m), 6.80 (1H, m) |

TABLE 3

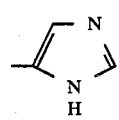

| R1 | R2 | R4 | NMR: cyclopropyl signals (δ, TMS) |
|---|---|---|---|
| CO2Me | m-NO2—C6H4 | C6H5 | 1.50 (broad octet, 4H) |
| CN | m-Cl—C6H4 | C6H5 | 1.60 (m, 4H) |
| COCH3 | o-CF3—C6H4 | C6H5 | 1.65 (m, 4H) |
| CO2Me | β-pyridyl | C6H4—p-Cl | 1.75 (m, 4H) |
| CO2Et | m-NO2—C6H4 | C6H4—p-OH | 1.50 (m, 2H), 1.95 (m, 2H) |
| CO2Me | m-NO2—C6H4 | C6H4—p-NH2 | 1.50 (m, 4H) |
| COC6H5 | m-Cl—C6H4 | C6H4—p-NO2 | 1.70 (m, 4H) |
| CO2Et | m-CF3—C6H4 | β-pyridyl | 1.50 (m, 2H), 1.80 (m, 2H) |
| CO2Me | o-NO2—C6H4 | [pyrrolyl] | 1.57 (m, 2H), 2.2 (m, 2H) |

EXAMPLE 6

A solution of 2-[2-(4-acetoxy-3-methoxy-5-N-morpholinomethyl)phenyl]ethenyl-3,5-dicarboethoxy-4-(m-nitrophenyl)-6-methyl-1,4-dihydropyridine (3.2 g) and lithium hydroxide monohydrate (0.8 g) in EtOH (50 ml) is stirred at room temperature for 30 minutes, then it is neutralized with an aqueous solution of NaH2PO4, filtered and the eluate evaporated to dryness. The residue, dissolved in AcOEt (50 ml), is washed with water (3×15 ml), dried on Na2SO4, evaporated to dryness and crystallized from EtOH to give 2.4 g of 2-[2-(4-hydroxy-3-methoxy-5-N-morpholinomethyl)phenyl]ethenyl-3,5-dicarboethoxy-4-(m-nitrophenyl)-1,4-dihydropyridine, m.p. 148°–150° C.

EXAMPLE 7

Using the procedure described in Example 6 the following 6-methyl-3,5-dicarboethoxy-1,4-dihydropyridine derivatives are obtained:

2-[2-(4-hydroxy-3-methoxy)phenyl]ethenyl-4-(m-nitrophenyl); m.p. 178°–181° C.;

2-[2-(4-hydroxy-3-methoxy)phenyl]ethenyl-4-(m-chlorophenyl); oil;

2-[2-(4-hydroxy-3-methoxy)phenyl]ethenyl-4-(β-pyridyl); oil;

2-[2-(2-hydroxyphenyl)]ethenyl-4-(m-trifluoromethylphenyl); oil.

EXAMPLE 8

A solution of 2-[2-[4-(2-methoxyethoxy)methoxy-3-methoxy-5-(4-methyl-piperazin-1-yl)methyl]phenyl]ethenyl-3,5-dicarboethoxy-4-(m-nitrophenyl)-6-methyl-1,4-dihydropyridine (4.8 g) and trifluoroacetic acid (11 ml) in dichloromethane (150 ml) is stirred, under N2 atmosphere, for 4 hours, then it is evaporated under reduced pressure, the residue is partitioned between AcOEt (80 ml) and water (50 ml), neutralized with a saturated solution of NaHCO3, the organic layer washed with water (3×20 ml), dried on Na2SO4 and evaporated to dryness to give 3.5 g of 2-[2-[4-hydroxy-3-methoxy-5-(4-methylpiperazin-1-yl)methyl]phenyl]ethenyl-3,5-dicarboethoxy-4-(m-nitrophenyl)-6-methyl-1,4-dihydropyridine as an amorphous solid.

By treatment of a solution of the free base in a suitable solvent (e.g. AcOEt) with a solution of two molar equivalents of an acid (e.g. maleic and fumaric acid) the corresponding salts (dimaleate, m.p. 129°–130° C. and difumarate, m.p. 202°–204° C.) are obtained.

EXAMPLE 9

According to the procedure of Example 8, the following 6-methyl-3-carboethoxy-1,4-dihydropyridines derivatives are prepared:

2-[2-[4-hydroxy-3-methoxy-5-(4-methylpiperazin-1-yl)phenyl]ethenyl-5-cyano-4-(m-nitrophenyl);

2-[2-(4-hydroxy-3-methoxy-5-N-pyrrolidinomethyl)-phenyl]ethenyl-5-carboethoxy-4-(m-nitrophenyl);

2-[2-(4-hydroxy-3-methoxy-5-N-pyrrolidinomethyl)-phenyl]ethenyl-5-carbomethoxy-4-(m-trifluorophenylmethyl);

2-[2-(3-bromo-4-hydroxy-5-methoxy)phenyl]ethenyl-5-carboethoxy-4-(m-nitrophenyl);

2-[2-(2-mercaptophenyl)]ethenyl-5-carboethoxy-4-(m-chlorophenyl).

EXAMPLE 10

Sodium hydride (0.44 g, 80% oil dispersion) is washed with hexane under N2 atmosphere, then trimethylsulfoxonium iodide (3.2 g) and DMSO (15 ml) are added at 10÷15° C. under stirring. After 20 minutes a solution of 2-(2-phenyl)ethenyl-3,5-dicarboethoxy-4-(m-nitrophenyl)-6-methyl-1,4-dihydropyridine (6.5 g) in DMSO (15 ml) is added; the stirring is continued for one hour at 20° C. and for 4 hours at 50° C., then the solution is poured in iced water (250 ml), extracted with AcOEt (3×30 ml), washed with water (3×10 ml), dried on Na2SO4, evaporated to dryness and the residue purified by column-chromatography on silica gel (600 g; eluent Et2O/AcOEt 95/5) to give 0.37 g of 2-(2-phenyl-1-cyclopropyl)-3,5-dicarboethoxy-4-(m-nitrophenyl)-6-methyl-1,4-dihydropyridine as an amorphous solid having identical NMR, IR and UV spectra with the compound described in Example 3.

EXAMPLE 11

A mixture of 2-(4-hydroxy-3-methoxyphenyl)ethenyl-3-carboethoxy-5-carbomethoxy-4-(m-chlorophenyl)-6-methyl-1,4-dihydropyridine (1 g), formaldehyde (0.2 g) and diethylamine (0.3 g) in EtOH:H2O (8:2, 30 ml) is heated to the reflux temperature for 3 hours, evaporated to dryness. The residue is partitioned between AcOEt and water, the organic phase is dried on Na2SO4, evaporated to dryness to give after SiO2 column chromatographic purification 2-(5-diethylaminomethyl-4-hydroxy-3-methoxyphenyl)ethenyl-3-carboethoxy-5-carbomethoxy-4-(m-chlorophenyl)-6-methyl-1,4-dihydropyridine (as an oil, hydrochloride m.p. 158°-160° C.).

An aqueous solution of 0.3 g of the hydrochloride salt is boiled with an excess of imidazole (0.15 g) until ceased the evolution of diethylamine. The mixture is evaporated to dryness and after the usual work-up 0.12 g of 2-[5-(imidazol-1-yl)methyl-4-hydroxy-3-methoxyphenyl)ethenyl-3-carboethoxy-5-carbomethoxy-4-(m-nitrophenyl)-6-methyl-1,4-dihydropyridine as a viscous oil are obtained.

We claim:

1. A compound of the formula I

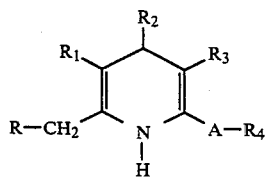

wherein

R is hydrogen or $C_1$–$C_5$ lower alkyl;

$R_1$ is a member selected from the group consisting of acetyl, benzoyl, cyano, nitro, free or esterified carboxy group of formula $CO_2R_5$, and amide of formula —$CONR_6R_7$;

$R_2$ represents:
(a) a phenyl groupd unsubstituted or substituted by one or more $C_1$–$C_6$ alkyl, $C_1$–$C_6$ alkoxy, halo-$C_1$–$C_6$ alkyl, halo-$C_1$–$C_6$ alkoy, halogen, nitro, cyano, $C_1$–$C_6$ alkoxycarbonyl, $C_1$–$C_6$ alkylthio, $C_1$–$C_6$ alkylsulphinyl groups;
(b) pentafluorophenyl;
(c) α or β-naphthyl;
(d) a pyridyl, furanyl or thienyl group;
(e) α-benzo[2,3-b]-1,4-dioxane; or
(f) α-benzo[3,4-c]-furoxanyl;

$R_3$ is a free or esterified carboxy group of formula $CO_2R_5$;

A is a group of formula

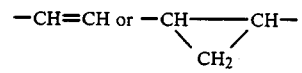

in cis or in trans form;

$R_4$ is a member selected from the group consisting of:
(a) a phenyl ring unsubstituted or substituted by at least one halogen, hydroxy, mercapto, $C_1$–$C_4$ alkoxy, $C_1$–$C_4$ alkylthio, $C_2$–$C_{12}$ acyloxy, imidazol-1-yl, —$NO_2$, amino, monoalkylamino selected from the group consisting of methyl amino, ethyl amino, isopropyl amino and benzyl amino, or dialkylamino selected from the group consisting of dimethyl amino, diethyl amino, benzyl-methyl amino, and a group of formula

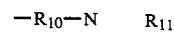

wherein $R_{10}$ is methyl, and $R_{11}$ forms with the N atom to which $R_{11}$ is connected a heterocyclic ring selected from the group consisting of pyrrolidin-1-yl, piperidin-1-yl, piperazin-1-yl, morpholin-4-yl, 4-methyl-piperazin-1-yl, 4-methyl-pyrazine-1-yl, imidazol-1-yl, 2-methoxycarbonyl-pyrrolidin-1-yl;
(b) an unsubstituted or substituted five or six-membered aromatic heteromonocyclic ring containing at least one S, O or N atom in the ring and attached to the dihydropyridine ring through a carbon atom of said aromatic hetermonocyclic ring, said substituted five or six-membered aromatic heteromonocyclic ring being substituted by at least one hydroxy, $C_1$–$C_4$ alkoxy, amino, carboxyamido, acetoxy or $C_1$–$C_4$ alkyl;

—$R_5$ is hydrogen; a $C_1$–$C_6$ alkyl chain unsubstituted or substituted by at least one hydroxy, amino, monoalkylamino selected from the group consisting of methyl amino, ethyl amino, isopropyl amino and benzyl amino, dialkylamino selected from the group consisting of dimethyl amino, diethyl amino, benzyl-, methyl amino, and a group of formula

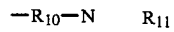

wherein $R_{10}$ is methyl, and $R_{11}$ forms with the N atom to which $R_{11}$ is connected a heterocyclic ring selected from the group consisting of pyrrolidin-1-yl, piperidin-1-yl, piperazin-1-yl, morpholin-4-yl, 4-methyl-piperazin-1-yl, 4-methyl-pyrazin-1-yl, imidazol-1-yl, 2-methoxycarbonyl-pyrrolidin-1-yl, or $C_1$–$C_6$ alkoxy; $C_3$–$C_6$ alkenyl; phenyl; phenyl(-$C_1$–$C_4$)alkyl; an ammonium or alkaline earth metal cation;

$R_6$ and $R_7$, which are the same of different, may be hydrogen, $C_1$–$C_6$ alkyl, benzyl, or phenyl; its non-toxic salts, enantiomers, diastereoisomers or mixtures thereof.

2. A compound according to claim 1, wherein A is a double bond in cis or trans form.

3. A compounds according to claim 1, wherein A is a cyclopropyl residue in cis or trans form.

4. A compound according to claim 1, wherein $R_2$ is selected in the group consisting of m-nitrophenyl, o-nitrophenyl, o-methylthiomethyl, m-trifluoromethylphenyl, o-trifluoromethylphenyl, o-chlorophenyl, m-chlorophenyl, β-pyridyl.

5. A compound according to claim 1, wherein R is hydrogen, $R_1$ and $R_3$ are lower alkoxycarbonyl groups.

6. A compound according to claim 1, selected from the group consisting of:

2-(2-phenylethenyl)-3,5-dicarboethoxy-4-(m-nitrophenyl)-6-methyl-1,4-dihydropyridine;

2-[2-(4-hydroxyphenyl)ethenyl]-3,5-dicarboethoxy-4-(m-nirophenyl)-6-methyl-1,4-dihydropyridine;

2-[2-(4-hydroxy-3-methoxyphenyl)-ethenyl]-3,5-dicarboethoxy-4-(m-nitrophenyl)-6-methyl-1,4-dihydropyridine;

2-(2-phenylethenyl)-3,5-dicarboethoxy-4-(o-trifluoromethylphenyl)-6-methyl-1,4-dihydropyridine;

2-(2-phenylethenyl)-3,5-dicarboethoxy-4-(2-methylthiophenyl)-6-methyl-1,4-dihydropyridine;

2-[2-(3-methoxy-4-hydroxy-5-N-morpholinomethylphenyl)ethenyl]-3,5-dicarboethoxy-4-(m-nitrophenyl)-6-methyl-1,4-dihydropyridine;

2-[2-(4-imidazol-1-yl-phenyl)-ethenyl]-3,5-dicarboethoxy-4-(m-nitrophenyl)-6-methyl-1,4-dihydropyridine;

2-[2-(3-methoxy-4-hydroxy-5-N-pyrrolidinomethylphenyl)ethenyl]-3,5-dicarboethoxy-4-(m-nitrophenyl)-6-methyl-1,4-dihydropyridine;

2-[2-(3-methoxy-4-hydroxy-5-imidazol-1-yl-methylphenyl)-ethenyl]-3,5-dicarboethoxy-4-(m-nitrophenyl)-6-methyl-1,4-dihydropyridine;

2-(2-phenylethenyl)-3-carboethoxy-5-cyano-4-(m-nitrophenyl)-6-methyl-1,4-dihydropyridine;

2-(2-phenylethenyl)-3-carboethoxy-5-nitro-4-(m-trifluoromethylphenyl)-6-methyl-1,4-dihydropyridine;

2-(2-mercaptophenylethenyl)-3,5-dicarboethoxy-4-(m-chlorophenyl)-6-methyl-1,4-dihydropyridine;

2-[2-(3-pyridyl)ethenyl]-3,5-dicarboethoxy-4-(m-nitrophenyl)-6-methyl-1,4-dihydropyridine;

2-[2-(3-methyl-2-thienyl)-ethenyl]-3,5-dicarboethoxy-4-(m-nitrophenyl)-6-methyl-1,4-dihydropyridine;

2-(2-phenyl-1-cyclopropyl-3,5-dicarboethoxy-4-(m-nitrophenyl)-6-methyl-1,4-dihydropyridine;

2-[2-(3-pyridyl)-1-cyclopropyl]-3,5-dicarboethoxy-4-(m-trifluoromethyl)-6-methyl-1,4-dihydro-pyridine;

2-[2-(4-hydroxyphenyl)-1-cyclopropyl]-3,5-dicarboethoxy-4-(m-nitrophenyl)-6-methyl-1,4-dihydropyridine.

7. A pharmaceutical composition for radical scavenging therapy, comprising a therapeutically effective amount of a compound of claim 1, 2, 3, 4, 5, or 6 and a pharmaceutically acceptable carrier.

* * * * *